(12) United States Patent
Poornaprajna et al.

(10) Patent No.: US 7,122,687 B2
(45) Date of Patent: Oct. 17, 2006

(54) PROCESS FOR THE PRODUCTION OF AN IMMUNOSUPPRESSANT

(75) Inventors: Acharya Poornaprajna, Karnataka (IN); Gopeekrishnan Sreenilayam, Karnataka (IN); Sambasivam Ganesh, Karnataka (IN)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 332 days.

(21) Appl. No.: 10/485,760

(22) PCT Filed: Aug. 29, 2002

(86) PCT No.: PCT/IN02/00178

§ 371 (c)(1),
(2), (4) Date: Feb. 3, 2004

(87) PCT Pub. No.: WO2004/020426

PCT Pub. Date: Mar. 11, 2004

(65) Prior Publication Data

US 2005/0165243 A1    Jul. 28, 2005

(51) Int. Cl.
  *C07D 307/00*    (2006.01)
  *C07D 307/78*    (2006.01)
  *C07D 307/87*    (2006.01)
  *C07D 307/93*    (2006.01)
  *C07D 407/00*    (2006.01)

(52) U.S. Cl. ...................... 549/305; 549/307
(58) Field of Classification Search ............. 514/233.5, 514/211, 212, 218, 226.8, 228.2, 253, 256, 514/320, 422; 549/305, 307
See application file for complete search history.

(56) References Cited

U.S. PATENT DOCUMENTS 4,727,069 A * 2/1988 Nelson et al. ......... 514/211.01
5,177,072 A * 1/1993 Nelson et al. ........... 514/233.5

* cited by examiner

*Primary Examiner*—D. Margaret Seaman
*Assistant Examiner*—Niloofar Rahmani
(74) *Attorney, Agent, or Firm*—Stacy L. Blasberg; Sam Pastemack

(57) ABSTRACT

In one aspect, the present invention provides a process for producing a sodium salt of an immunosupressant of Formula I

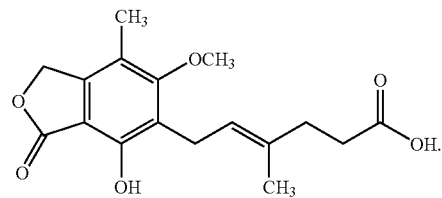

Formula I 5 Claims, No Drawings

PROCESS FOR THE PRODUCTION OF AN IMMUNOSUPPRESSANT

PRIORITY CLAIM

The present application claims the benefit under 35 U.S.C. § 371 of International Application No.: PCT/IN02/00178, filed Aug. 28, 2002, the entire contents of this application is hereby incorporated herein by reference.

FIELD OF THE INVENTION

In one aspect, the present invention provides a method for producing a sodium salt of a compound of Formula I

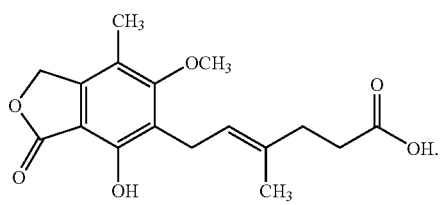

Formula I

BACKGROUND OF THE INVENTION

Mycophenolic acid is an immunosuppressive agent that inhibits de novo purine nucleotide synthesis via inhibition of IMP dehydrogenase and prevents the formation of XMP and GMP.

Mycophenolic acid sodium salt or ERL 080 has been widely discussed in available patent and non-patent literature, for its use in treatment of diseases and transplantation.

The use of Mycophenolalic acid sodium salt in the treatment of hyperuricaemia has been reported in U.S. Pat. No. 3,705,946. U.S. Pat. No. 6,025,391 describes an enteric coating composition, containing HPMC phthalate and triacetin prepared for capsules containing monosodium mycophenolate, and adapted to release mycophenolate in the upper part of the intestinal tract.

The tolerability profile of sodium mycophenolate and mycophenolate mofetil with and without cyclosporin has been discussed in Toxicology 157(2001) 207–215.

The Journal Acta Crystallographica, Section C: Crystal Structure Communications (2000), C56(4), 432–433, discusses a crystal stucture of sodium mycophenolate.

SUMMARY OF THE INVENTION

In one aspect, the present invention discloses a process for the manufacture of the sodium salt of a compound of Formula I

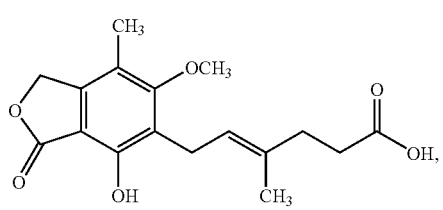

Formula I comprising reacting the compound of Formula I with an aqueous solution of sodium hydroxide, sodium carbonate or sodium bicarbonate, or a C2 to C10 carboxylic acid sodium salt. In one embodiment, the compound of Formula I

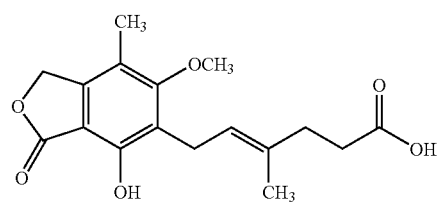

Formula I is reacted with sodium acetate, sodium 2-ethyl hexanoate or sodium caprylate.

In another aspect, the present invention provides a process for the manufacture of a sodium salt of a compound of Formula I

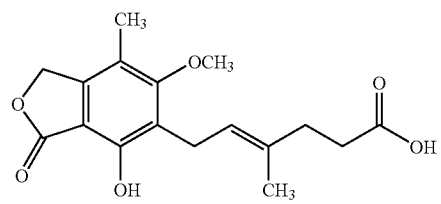

Formula I comprising converting the compound of Formula I to its ammonium or dibenzamide form and reacting it with an aqueous solution of sodium hydroxide or a $C_2$ to $C_{10}$ carboxylic acid sodium salt. In one embodiment, the $C_2$–$C_{10}$ carboxylic acid sodium salt is sodium acetate, sodium 2-ethyl hexanoate or sodium caprylate.

DETAILED DESCRIPTION OF PREFERRED EMBODIMENTS OF THE INVENTION

In one aspect, the present invention describes a process of manufacturing a sodium salt of a compound of Formula I

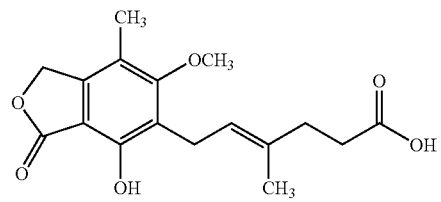

Formula I by reacting the compound of Formula I with an aqueous solution of sodium hydroxide, sodium hydroxide derivatives, or a $C_2$ to $C_{10}$ carboxylic acid sodium salt.

In another aspect, the compound of Formula I

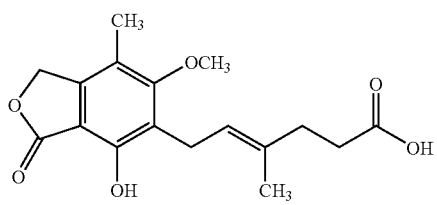

Formula I may be converted to an ammonium salt or a dibenzyl amide salt before it is converted to the corresponding sodium salt.

In one embodiment, the compound of Formula I

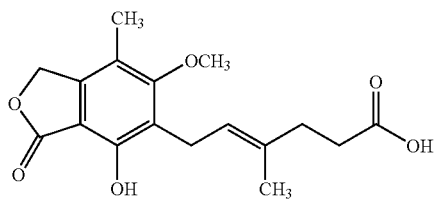

Formula I is converted to its ammonium salt by treatment with ammonia.

In another embodiment, a dibenzyl amide form of the compound of Formula I

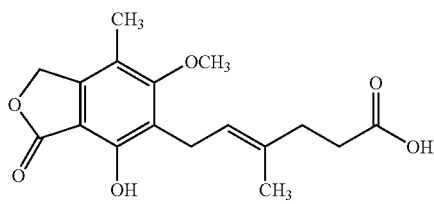

Formula I is obtained by reaction with dibenzyl amine.

In other embodiments, the $C_2$ to $C_{10}$ carboxylic acid sodium salt is selected from the group consisting of sodium acetate, sodium 2-ethyl hexanoate and sodium caprylate. In certain other embodiments, the sodium hydroxide derivatives are selected from the group consisting of $Na_2CO_3$ and $NaHCO_3$.

In certain embodiments, the invention provides a process for the manufacture of the sodium salt of a compound of Formula I:

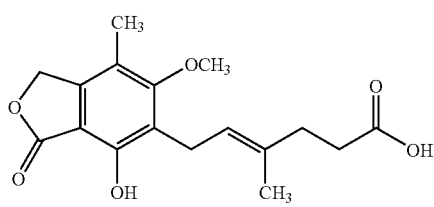

Formula I comprising reacting the compound of formula I with an aqueous solution of sodium hydroxide, sodium carbonate or sodium bicarbonate, or a C2 to C10 carboxylic acid sodium salt. Exemplary C2–C10 carboxylic acid sodium salts include sodium acetate, sodium 2-ethyl hexanoate and sodium caprylate.

In a further aspect, a compound of Formula I

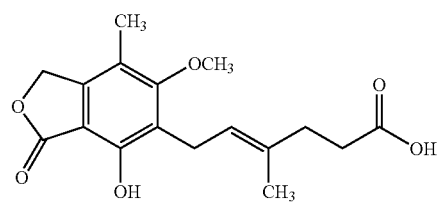

Formula I may be converted to its ammonium salt by reacting it with ammonia. The resulting ammonium salt may be reacted with an aqueous solution of sodium hydroxide, sodium acetate, sodium 2-ethyl hexanoate or sodium caprylate to form the corresponding sodium salt.

Alternatively, the compound of Formula I

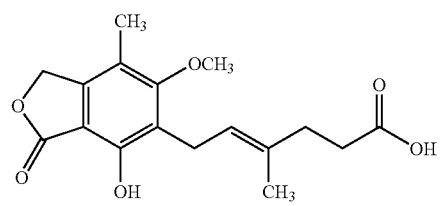

Formula I may be converted to its dibenzamide form by reaction with dibenzylamine. Subsequent reaction with an aqueous solution of sodium hydroxide, sodium acetate, sodium 2-ethyl hexanoate or sodium caprylate leads to the formation of the sodium salt of the I corresponding sodium salt.

The following Examples further illustrate the invention, with the understanding that the invention is not intended to be limited by the details disclosed therein.

EXAMPLE 1

13.5 g of sodium hydroxide is dissolved in 75 ml of methanol. 100 g of micophenolic acid was added, and the resulting solution was stirred for half an hour at room temperature (RT). The is reaction mixture was chilled to 10° C. and the solid was filtered. The solid was washed with 50 ml acetone and dried under vacuum at 40 to 50° C. A final yield 90% (95 g) was observed.

EXAMPLE 2

To a solution of 10 g of sodium acetate in 55 ml of methanol, 74 g of micophenolic acid was added and the resulting solution was stirred for half an hour at RT. The reaction mixture was chilled to 10° C. and the solid was filtered. The solid was washed with 50 ml acetone and dried under vacuum at 40 to 50° C. A final yield 90% (95 g) was observed.

EXAMPLE 3

Dicyclohexyl amine was added to a slurry of mycophenolic acid (25 g) in methanol, and the resulting mixture was stirred at RT. The precipitated solid was treated with aqueous sodium hydroxide solution under stirring at RT. The reaction mixture was cooled to −10° C. and the precipitated solid was filtered and dried.

We claim:
1. A process of manufacturing a sodium salt of a compound of Formula I

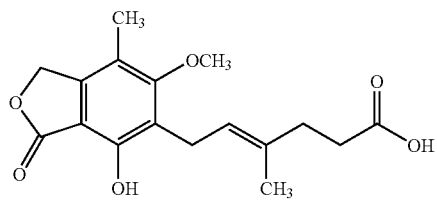

Formula I comprising reacting the compound of Formula I with a $C_2$ to $C_{10}$ carboxylic acid sodium salt.

2. The process of claim 1, wherein the compound of Formula I

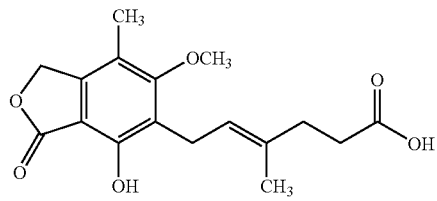

Formula I is converted to an ammonium salt or a dibenzyl amide salt before it is converted to the sodium salt.

3. The process of claim 2, wherein the compound of Formula I is converted to its ammonium salt by treatment with ammonia.

4. The process of claim 2, wherein the compound of Formula I is converted to its dibenzyl amide form by reaction with dibenzyl amine.

5. The process of claim 1, wherein the $C_2$ to $C_{10}$ carboxylic acid sodium salt is selected from the group consisting of sodium acetate, sodium 2-ethyl hexanoate and sodium caprylate.

* * * * *

UNITED STATES PATENT AND TRADEMARK OFFICE
CERTIFICATE OF CORRECTION

PATENT NO. : 7,122,687 B2  Page 1 of 1
APPLICATION NO. : 10/485760
DATED : October 17, 2006
INVENTOR(S) : Acharya Poomaprajna, Gopeekrishnan Sreenilayam and Sambasivam Ganesh It is certified that error appears in the above-identified patent and that said Letters Patent is hereby corrected as shown below:

On the title page of the patent the Assignee item 73 should read Biocon Limited, Bangalore, India (IN) not Sunesis Pharamcueticals, Inc, South San Francisco, CA (US).

Signed and Sealed this

Twelfth Day of February, 2008

JON W. DUDAS
*Director of the United States Patent and Trademark Office*